United States Patent [19]

Gellert

[11] 4,239,043
[45] Dec. 16, 1980

[54] ABSORBENT MEANS FOR CATAMENIAL DEVICES

[75] Inventor: Dale A. Gellert, Aurora, Ind.

[73] Assignee: The Procter & Gamble Company, Cincinnati, Ohio

[21] Appl. No.: 964,842

[22] Filed: Nov. 29, 1978

[51] Int. Cl.³ .............................................. A61F 13/20
[52] U.S. Cl. ..................................... 128/285; 428/314
[58] Field of Search ............................... 128/155–156, 128/284, 285, 287, 290 R, 296; 428/310–311, 314, 315

[56] References Cited

U.S. PATENT DOCUMENTS

| | | | |
|---|---|---|---|
| 3,024,207 | 3/1962 | Shaw et al. | 128/290 R |
| 3,463,745 | 8/1969 | Hofrichter et al. | 128/284 |
| 3,815,601 | 6/1974 | Schaefer | 128/285 |
| 3,900,030 | 8/1975 | Bashan | 128/285 |
| 3,994,298 | 11/1976 | DesMarms | 128/285 |

Primary Examiner—C. Fred Rosenbaum
Attorney, Agent, or Firm—Fredrick H. Braun; Richard C. Witte

[57] ABSTRACT

The object of the invention is to provide an improved absorbent means that can be used in a catamenial device.

The improved absorptive means comrpises a foam means having an absorbency improvement means at least arrayed on the surface of the foam means wherein the absorbency improvement means is adherent to the foam, hydrophilic, and has a high surface area. The foam means is preferably cut into small blocks made of hydrophilic polyester foam or hydrophilic polyurethane foam. Absorbency improvement means is preferably cellulose fibers.

A tampon incorporating the improved absorbent means has overwrap 11 containing an aggregate absorbent body 12 comprising foam blocks coated with fibrous material 16 and ancillary absorbent material 17. The overwrap 11 is sealed by a side seam 13 and knotted at one end with a withdrawal string 15. The fiber coated foam blocks offer improved rate of absorbency, volume of absorbency, and retention of liquid under pressure due to more efficient utilization of the maximum absorbent capacity of the tampon. The fibrous coating of the foam blocks functions to wick liquid between a plurality of hydrophilic foam blocks and into the center of the foam blocks.

8 Claims, 5 Drawing Figures

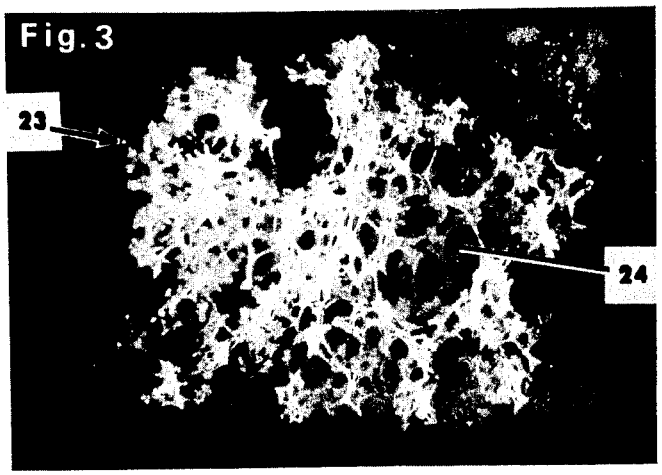
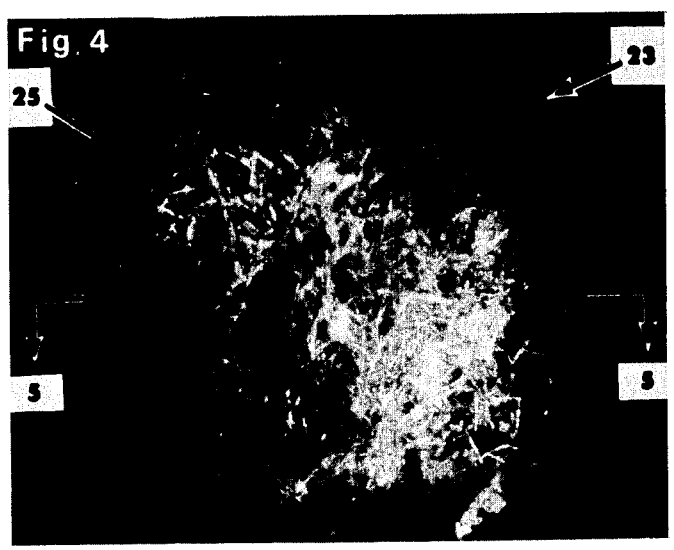
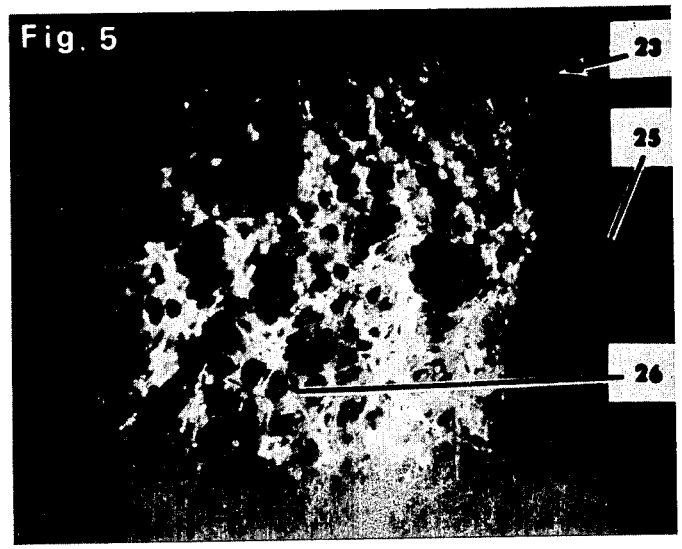

4,239,043

ABSORBENT MEANS FOR CATAMENIAL DEVICES

TECHNICAL FIELD

This invention relates to improved absorbent means and particularly to improved absorbent means for use in catamenial devices.

Absorbent means incorporated into catamenial devices, such as tampons, must be highly absorbent, have a high rate of absorbency to prevent any leakage of menses passing by the tampon in vivo and also retain absorbed moisture under pressure. The tampon must absorb enough menses to be left in place for a substantial amount of time to eliminate withdrawal discomfort and uneconomical replacement costs. The tampon must also retain absorbed menses when subjected to intravaginal pressure or to prevent leakage while in use during physical activity by the wearer.

BACKGROUND ART

U.S. Pat. No. 3,815,910 issued to Schaefer on June 11, 1974 discloses a catamenial tampon having a liquid pervious overwrap and an aggregate absorbent body. Schaefer discloses an aggregate absorbent body made of discrete foam bits shaped as cubes and, in a preferred embodiment, an ancillary absorbent material defined to be super absorber CLD, cross-linked carboxymethyl cellulose. Schaefer does not disclose use of an improved absorbent means wherein foam blocks are coated with an absorbency improvement means, such as fibrous material.

U.S. Pat. No. 3,122,140 issued to Crowe on Feb. 25, 1964, U.S. Pat. No. 3,122,141 issued to Crowe on Feb. 25, 1964, and U.S. Pat. No. 3,156,242 issued to Crowe on Nov. 10, 1964, disclose various absorbent bandage devices having a flexible sheet of cellulose sponge material, a layer of absorbent other than textile length fibers, and textile length fibers pierced through the cellulose sponge material to contact the wound surface. In the Crowe patents, the cellulose fibers extending through the cellulose sponge material act to wick body fluids from the surface of a wound through the cellulose sponge and into the nontextile length fiber absorbent material. The Crowe patents do not claim an improved absorbent material using a hydrophilic foam material whose surface is covered with fibrous absorbency improvement means which wick liquid both into and around hydrophilic foam means.

U.S. Pat. No. 3,900,030 issued to Basham on Aug. 19, 1975 discloses a tampon having an absorptive body of hydrophilic polyurethane foam containing from about 15 to 30 percent by weight of finely divided, water-swellable polymer. The Basham patent does not have an aggregate absorbent body of a plurality of foam blocks and does not use an absorbency improvement means such as cellulose fibers.

U.S. Pat. No. 3,695,270 issued to Dostal on Oct. 3, 1972 discloses a tampon having two absorbent layers wherein one of the layers is made of an absorbent filament and the other is of an absorbent material containing a plurality of holes. The filaments in Dostal are directed through the holes of the absorbent layer in a direction transverse to the body of the tampon. The filaments bind together the layers of absorbent material and help wick menses through the layers of absorbent material. The absorbent material in Dostal does not include a hydrophilic foam material coated by a fibrous absorbency improvement means. The fibers used in Dostal bind together and penetrate an absorbent sheet and not a foam means.

U.S. Pat. No. 3,999,549 issued to Poncy on Dec. 28, 1976 discloses a tampon having a core of highly absorbent, noncompressible fibrous material surrounded by a sheet of resilient, open cell hydrophilic foam which is liquid transmissive. The foam sheet acts as a cushioning element to make the tampon more comfortable and to transmit liquid through the foam to the absorbent core. Poncy does not disclose blocks of hydrophilic foam coated with fibrous material to improve the absorbency nor does it teach a plurality of absorbent materials used in an aggregate body of a tampon.

None of the above disclosed background patents teach an improved absorbent means made from blocks of foam means coated on the surface with an absorbency improvement means. Furthermore, none of the disclosed background art teaches use of a plurality of such absorbent means in an overwrap to create an absorbent catamenial such as a tampon.

DISCLOSURE OF THE INVENTION

In accordance with the present invention, an improved absorbent means is provided comprising a foam means and an absorbency improvement means at least arrayed on the surface of the foam means. The absorbency improvement means comprises an inherently hydrophilic material having a high surface area.

In accordance with the invention, the absorbent material preferably is a foam means made of hydrophilic foam. Further, the hydrophilic foam is one of a group of polyester or polyurethane foam.

In accordance with the invention, the absorbency improvement means is a fibrous material, such as cellulose fibers. The cellulose fiber having an average fiber length of at least 1.0 millimeters and a diameter of 15-45 microns, preferably with a length of 2.5 millimeters and a diameter of 35-45 microns.

In accordance with the invention, the foam means are shaped as blocks having a maximum edge dimension of 1/16 to one inches (0.16 to 2.54 cm.) and preferably ⅛ to ⅜ inches (0.32 to 0.95 cm.).

In accordance with the present invention, an absorptive device is provided comprising an aggregate of individual pieces of absorbent foam means and an ancillary absorbent material. The foam means is coated at least on the surface with an absorbency improvement means and the aggregate is entirely encased within a flexible fluid permeable overwrap. None of the absorbent foam means protrudes through the exterior portion of the overwrap. The aggregate is flexible and resilient to produce an absorbent device that is soft, highly compressible, comfortable and resilient.

In accordance with the present invention, an absorptive device is provided comprising an absorptive tampon, a tubular inserter and an injection means for releasing the tampon from the inserter into a body cavity. The tampon has an aggregate absorbent body comprising individual pieces of absorbent foam means and ancillary absorbent material contained within a flexible fluid permeable overwrap, such that substantially none of the aggregate absorbent body protrudes through the exterior portion of the overwrap leaving the exterior surface of the tampon as the overwrap. The foam means are coated, at least on the surface, with an absorbency improvement means. The tampon is resiliently compacted within the inserter whereby the tampon is easily ejectable and fluffs out rapidly after an in vivo ejection from the inserter to fill the vaginal cross section.

DESCRIPTION OF THE DRAWINGS

The attached drawings are described below:

FIG. 3 is a side view of a hydrophilic foam block at 10×;

FIG. 4 is a side view of an improved absorbent means that is the subject of the invention at 10×; and FIG. 5 is a side cross-sectional view of FIG. 4 along section line 5—5.

DESCRIPTION OF THE INVENTION

The invention disclosed herein is an absorbent material that absorbs an increased volume of liquid, has a high rate of absorbency and holds the liquid better under pressure than conventional absorbent materials.

The absorbent material disclosed herein can be used alone or in absorbent articles. This absorbent material is particularly useful in catamenials, for example tampons, which must absorb large amounts of menses and hold it for protracted periods of time under intravaginal pressure.

The absorbent material disclosed herein is an absorbent foam means having an absorbency improvement means arrayed on the surface of the foam means. The absorbency improvement means is a hydrophilic material having a high surface area that is adherent to the surface of the foam means.

In one preferred embodiment of the invention, the foam pieces are made of reticulated hydrophilic polyester foam or reticulated hydrophilic polyurethane foam.

In another preferred embodiment of the invention, the absorbency improvements means is a fibrous material. It is particularly desirable to use cellulose fibers because of their high availability, low cost and desirable wicking ability.

Figure 1:
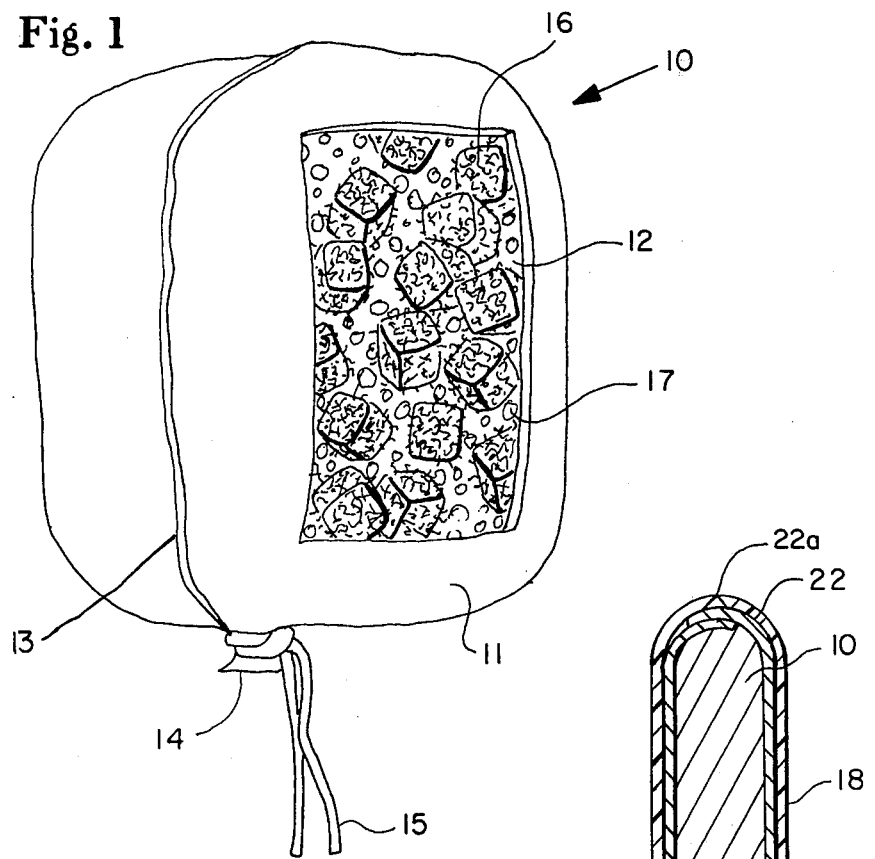
FIG. 1 is a perspective view of a tampon of the present invention having a section of the overwrap cut away to expose the aggregate absorbent material.
Figure 2:
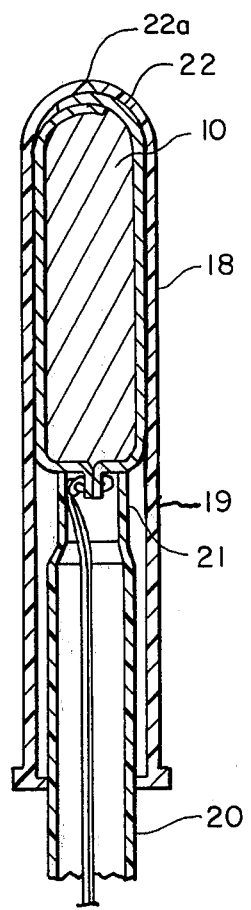
FIG. 2 is a side cross-sectional elevation of a tampon enclosed within an inserter.

The absorbent material can be used as a part of the aggregate absorbent body of a tampon as seen in FIG. 1. The absorbent material can be used in a tampon such as that disclosed in U.S. Pat. No. 3,815,601, Catamenial Aggregate Absorbent Body, issued to Schaefer on June 11, 1974 which is hereby incorporated by reference.

Referring to FIG. 1, tampon 10 has a moisture pervious overwrap 11 containing an aggregate absorbent body 12. The aggregate absorbent body 12 is contained within the moisture pervious overwrap 11. The overwrap 11 is sealed with a side seam 13 and a gathered end 14 secured by knotted withdrawal string 15. The aggregate absorbent body 12 comprises fiber coated foam blocks 16 and approximately ⅛" square pieces of ancillary absorbent material 17, such as cross-linked carboxymethyl cellulose, CLD. The element CLD is described and disclosed in U.S. Pat. No. 3,678,031, Slurry Process for the Production of Absorptive Carboxy Methyl Cellulose Fibers, issued to Schoggen on June 29, 1971 which is hereby incorporated by reference. The overwrap 11 securely contains all elements of the aggregate absorbent body 12 within it, allowing no foam pieces or CLD to protrude through the overwrap 11.

Tampon 10 is inserted in the vagina with inserter 18. Inserter 18 has an outer tube 19 containing tampon 10 and ejector means 20. Tampon 10 is positioned inside outer tube 19 between the forward end 21 of plunger 20 and the forward end 22 of outer tube 19. Plunger 20 is axially mounted in outer tube 19 for telescoping movement to eject the tampon 10 into the vagina for use. The forward end 22 of outer tube 19 has a rounded shape to allow for easy entrance into the vagina. Forward end 22 is cut into a plurality of triangular segments that flex at the base near the intersection with the cylindrical portion of outer tube 19 and close with the apices of all sections meeting at point 22a. The triangular segments open to allow passage of the tampon into the vagina as the plunger 20 is moved telescopically forward relative to outer tube 10 to eject the tampon.

The absorbent material is preferably made from a hydrophilic foam. A particularly preferred embodiment of the invention uses hydrophilic polyester foam or polyurethane foam. This polyester foam material and process to make the foam are described in detail in U.S. Pat. No. 4,110,276, Polyester Foam Materials, issued to Thomas DesMarais on Aug. 29, 1978, which is hereby incorporated by reference.

One method to make the polyester foam is a batch method described below. In a 55,000 gallon (208 cu. meter) tank, the following components are added and mixed for five hours at 50°-55° C.: 100 parts Polyol [a block copolymer of polypropylene-glycol and polyethylene glycol initiated from pentaerythritol commercially available as BASF Wyandotte Pluracol P-747 available from BASF Wyandotte Corp., Industrial Chemical Group, Wyandotte, Mich. 48192]; 1 part surfactant [commercially available as BASF Wyandotte Pluronic L92 from BASF Wyandotte Corp., Industrial Chemical Group, Wyandotte, Mich. 48192]; 50 parts sodium carbonate; and 37 parts cross-linker [essentially tetrapropoxylated-pentaerythritol, commercially available as BASF Wyandotte PEP 450 from BASF Wyandotte Corp., Industrial Chemical Group, Wyandotte, Mich. 48192]. This mixture is then dehydrated for 3–4 hours at 120° C. The dehydrated mixture is mixed with 101 parts adipyl chloride. The resulting mixture is then fed to a conveyor where it is foamed at 100° C. under a vacuum of one inch (2.54 cm.) mercury. This process produces a polyester foam with a density of 2,.6–3.1 lbs/ft$^3$ (42–50 kgs/cu. meter).

Another preferred foam material is hydrophilic polyurethane foam. This foam and process for making it are more fully described in U.S. Pat. No. 4,067,832, Flexible Polyurethane Foam, issued to Thomas DesMarais on Jan. 10, 1978 and hereby incorporated by reference. Other suitable hydrophilic materials may be used to make the absorbent material of this invention.

The hydrophilic material is cut into particles. In a preferred embodiment, the foam is cut into cube-shaped blocks having a maximum edge dimension of 1/16 inches to one inch (0.16–2.54 cm.) and preferably ⅛ inches to ⅜ inches (0.32–0.95 cm.). The foam is cut into blocks by a conventional method.

The foam blocks are covered with an absorbency improvement means to improve wicking and retention of liquid absorbed. In a preferred embodiment of the invention, cellulosic fiber material is used. One example of such material is Foley Fluff available from Buckeye Cellulose Corporation, P.O. Box 8407, Memphis, Tenn. 38108. The fibers used are 1.0–2.5 mm in length and 15-45 microns in diameter and preferably average 2.5 mm in length and 35-45 microns in diameter.

Fibers used to coat the hydrophilic foam blocks have a high surface area and will readily adhere to the surface of reticulated foam, for example, bleached softwood communition pulp. The softwood pulp is dried to be air dry with up to 12% moisture by weight with a preferred moisture level of 6±1.5%. The softwood pulp has a preferred density of 0.5 to 0.6 grams per cubic centimeter, however, pulp of lower densities can also be used without affecting the properties of the final absorbent material.

When received in sheet form, the sheets must be disintegrated to separate the fibers from each other. In this case, a disintegrator made by Barth Industries, Inc., 12650 Brookpark Road, Cleveland, Ohio 44130, may be used. The disintegration mill is run at 3500-5500 rpm, at paper feed rates of 5 fpm to 150 fpm (1.5-46 meters/min.) with a preferred range of use of 20 to 40 fpm (6 to 12 meters/min.).

The hydrophilic foam blocks are coated with fibers in a mixer. In the mixer, two separate streams of foam blocks and fibers enter separately to be mixed. The blocks and fibers reside in the mixer long enough to assure homogeneous coating of the blocks with the fiber material yielding a homogeneous discharge of fiber coated foam blocks in a single stream. In a Marian mixer, a residence time of up to 30 seconds is preferred at about 50% full level, however, there may be a wide range of residence times and levels provided they produce a homogeneous discharge stream. Marian mixers are made by the Rapid Machine Company, 3575 Third Avenue, P.O. Box 286, Marions, Iowa 52302.

EXAMPLE

An example of the process to coat foam blocks with fibers is disclosed below wherein 455 pounds (206 kgs.) of polyester hydrophilic foam were coated with approximately 112 pounds (51 kgs.) of fiber at a rate of 5.9 pounds per minute (2.7 kgs/min.) yielding a product that is 19.5% fiber by weight. The polyester foam is properly sized and cut into cubes with a maximum edge diameter of one inch (2.54 cm.). The fiber is disintegrated Foley Fluff Dry Lap available from Buckeye Cellulose, Memphis, Tenn. The foam blocks are washed, dryed and dropped from a drying oven into a five cubic foot Marian Continuous Flow Paddle Mixer available from Rapid Machine Company. The paddle mixing shaft is rotated at approximately 167 rpm by a 0.5 horsepower motor. The foam blocks are mixed in a mixer for 20 seconds. Fibers are then added which are made by disintegrating the Foley Fluff Dry Lap. Disintegrated dry lap fibers are then fed directly through an exhaust chute of the disintegrator into the center of the mixer. The fiber and foam blocks are then mixed for about eight to ten seconds.

The foam blocks are coated with fiber as the foam and fiber are mixed as a direct result of the action of the paddle blades of the mixer. The paddle blades of the mixer lift and tumble the foam and fiber together in a figure eight pattern parallel to the shaft of the mixer with the paddles that achieves the desired cross blending action. Retention time in the mixer is largely controlled by paddle rpm and paddle shape which will direct the flow of foam and fiber through the mixing chamber. After the foam and fiber have mixed for a sufficient time to coat the foam blocks, the coated foam blocks are discharged through a hole in the end of the mixer opposite the material entrances into a screw conveyor which transfers material to a packing apparatus.

An uncoated hydrophilic foam block of the invention can be seen in FIG. 3. The foam block 23 has a vast plurality of voids 24 which provide fluid holding capacity. The absorbent material of the invention is a foam block having its surface coated with an absorbency improvement material, as seen in FIG. 4. In FIG. 4, a hydrophilic foam block 23 is coated with cellulose fibers 25, here dyed red for visual emphasis. As seen in FIG. 5, a side cross-sectional view of absorbent material of the invention, a foam block coated with fibrous material results in a foam block having substantially its entire surface coated with fibers and some fibers 26 penetrating into the interior of the cube.

The absorbent material of this invention shows improved wicking of liquid. The fibers on the surface of the foam blocks transport liquid between blocks when there are a plurality of blocks. Thus, absorbency of a plurality of fiber coated foam blocks is improved because liquid is distributed between blocks for more complete use of the absorptive capacity. The fibers which penetrate the foam blocks transport liquid by wicking into the center of the blocks to increase absorbency of individual fiber coated foam blocks. The fibers create capillary pathways between blocks and into the center of the blocks to wick liquid from foam block to foam block and into the interior of each block respectively.

The fibers 25 adhere to the surface of the hydrophilic foam blocks due to mechanical interaction between the roughened foam surface and the fibers. The roughened edges are created by the ruptured voids in the blocks.

The improved absorbent material of the present invention can be used, for example, as an element in the aggregate absorbent body of a tampon as disclosed in U.S. Pat. No. 3,815,601 issued to Schaefer, as mentioned above. Combining a plurality of foam means having absorbency improvement means, for example, the fiber coated foam blocks described above provide an excellent absorbent aggregate body for catamenials. A tampon having an absorbent core combining fiber coated foam blocks and ancillary absorbent material, such as CLD, shows improved rate of absorbency, improved volume of absorbency and an improved ability to retain absorbed liquid under pressure. The fiber coating on the foam blocks acts to aid in distribution of menses between the hydrophilic foam and ancillary absorbent material and to transport liquid into the center of each hydrophilic foam block. The improved wicking caused by the fiber will maximize utilization of the absorbent capacity of the entire aggregate absorbent body to allow the tampon to be more effective in absorbing menses. Thus, the fibers promote maximum uniform flow throughout the entire absorbent body, both to the absorbent hydrophilic foam and to the ancillary absorbent material, such as super absorbent CLD. Internal penetration of the foam by the fibers facilitates penetration of fluid into the internal structure of the foam, increasing the foam reservoir efficiency. The net result of the added fiber in the tampon structure as disclosed herein is to create increased capillary suction to draw menses into the tampon and improve menses distribution within the tampon.

A tampon containing the absorbent material of this invention has a polyester overwrap consisting of 2.5 denier spun bonded fibers with a basis weight of 0.5 oz./yd.$^2$ (12 gm/m$^2$). It contains an aggregate absorbent body containing polyester foam cubes coated with cellulose fibers and CLD. The bottom of the overwrap is gathered together and held by a knotted withdrawal string. The fiber coated foam blocks constitute 50-100 weight percent of the absorbent aggregate, and preferably 70-90 weight percent.

In an example of a tampon having an aggregate absorbent body, the body contained by weight percent:

Fiber Coated Foam—85%

CLD—15%

The foam cubes have an edge dimension of ¼±⅛ inches (0.64±0.32 cm.). The fibers in the fiber coating have an average fiber length of 2.5 mm. and an average diameter of 40 microns.

The performance characteristics of the improved absorbent material that is the subject of this invention were tested and the results are listed below in Table I. Tampons having an aggregate absorbent body of an ancillary absorbent material, CLD, and hydrophilic foam cubes coated with different amounts of fiber were tested for performance properties. The table below shows that as the percentage of fiber coating on the foam cubes in the aggregate absorbent body increases, the unrestrained wicking capacity of the tampon increased. Tests were performed for both super size tampons and regular size tampons. The unrestrained wicking capacity was tested by a drip cup wicking test method. In the drip cup wicking test, the absorbent capacity of the tampon is tested until it no longer accepts liquid and a standard amount of liquid overflows into a measured beaker. The liquid used was artificial menses to closely approximate actual in use conditions. The test is performed in a beaker having an artificial menses inlet, a sieve over the inlet to support the tampon, and an outlet to direct overflow of artificial menses into a measured beaker. A dry tampon is set into the beaker on top of the sieve and a 0.5 psi (26 mm Hg) load is applied to ensure contact of the tampon with the sieve. Artificial menses is then piped into the beaker through the menses inlet and through the sieve where it will be absorbed by the tampon. When the tampon no longer accepts menses as rapidly as it is being pumped into the beaker, the menses overflows through the menses outlet into the measuring beaker. The amount of artificial menses flowing in the inlet of the tampon loaded beaker is metered and measured to record total volume of menses fed to the beaker until 1 ml. of menses solution overflows to the measured beaker.

The total amount of artificial menses fed to the beaker is then measured and compared for various tampons. In Table I below, the fiber added is only added as a coating to the hydrophilic foam blocks. The table clearly shows that as the amount of fiber in the aggregate absorbent body increases, the unrestrained wicking capacity of the tampon increases.

The artificial menses used is a mixture of the following components:

24,640 ml. Distilled water 280 gm. Sodium chloride (NaCl)

112 gm. Sodium Carbonate ($Na_2CO_3$)

2800 gm. Glycerol (99% solution)

129 gm. Carboxymethyl cellulose

TABLE I

| | Sample | % Fiber | Foam Weight (g) | Fiber Weight (g) | CLD Weight (g) | Artificial Menses Weight Absorbed (g) |
|---|---|---|---|---|---|---|
| Super Size Tampon | 1 | 0 | 2.30 | 0 | 0.48 | 16.45 |
| | 2 | 15 | 1.95 | 0.35 | 0.48 | 18.18 |
| | 3 | 25 | 1.72 | 0.58 | 0.48 | 19.43 |
| | 4 | 35 | 1.49 | 0.81 | 0.48 | 20.65 |
| Regular Size Tampon | 1 | 0 | 1.70 | 0 | 0.33 | 11.9 |
| | 2 | 5 | 1.62 | 0.08 | 0.33 | 12.5 |
| | 3 | 15 | 1.45 | 0.25 | 0.33 | 15.2 |
| | 4 | 25 | 1.28 | 0.42 | 0.33 | 16.2 |

Tampons having the improved absorbent material that is the subject of the current invention also show an increased capacity to hold synthetic menses under pressure. In the test below, the only fiber added to the tampon coats the hydrophilic foam cubes and the weight percent and actual weight added of fiber is disclosed. Table II reveals the weight of the synthetic menses held under each listed pressure by both a conventional tampon and tampon containing fiber coated hydrophilic foam blocks. The figure in parentheses beside each weight figure for menses held indicates the weight of artificial menses held as a multiple of tampon weight under each pressure condition. Tests were carried out in a syngynga, which is an aritificial vagina. A syngyna comprises a cylindrical glass beaker having water inlets and outlets and a centrally located rubber bladder defining a centrally located water tight portion having a first larger opening and a second smaller opening. The larger first opening defined by the rubber bladder allows insertion of the tampon into the bladder and a second opening allows artificial menses to be wicked into the tampon.

The rubber bladder is entirely surrounded by water. Pressure applied to the bladder and its contents can be changed by changing water pressure. Water passes through the water inlets and outlets to vary pressure in the glass beaker to exert a uniform hydrostatic pressure on a tampon inserted into the rubber bladder. In the test, a dry unused tampon is inserted into the large opening of the rubber bladder so it is completely inside the rubber bladder which is surrounded by the water in the beaker. The tampon is fully loaded with artificial menses wicked into the tampon through the smaller second opening under one quarter psig (13 mm. Hg.) pressure. The amount of menses added is carefully metered and measured to determine tampon loading under 13 mm. Hg. The hydrostatic water pressure is then increased to one half psig (26 mm. Hg.), and the amount of artificial menses that is squeezed out of the tampon under pressure is measured, subtracted from that initially put into the tampon under 13 mm. Hg. pressure to yield a loading of menses under one half psig (26 mm. Hg.) pressure. Pressure is then raised to ¾ psig (39 mm. Hg.), and the amount of menses squeezed out of the loaded tampon is measured and subtracted from the amount of menses contained in the loaded tampon under one half psig (26 mm. Hg.) to yield an amount of menses held in the tampon at ¾ psig (39 mm. Hg.). Water pressure is then raised to one psig (52 mm. Hg.) and the amount of menses squeezed out of the tampon is measured and subtracted from the amount contained by the tampon under ¾ psig (39 mm. Hg.) to yield an artificial menses loading at one psig (52 mm. Hg.). This procedure is followed for both the tampon with fiber coated foam blocks and the tampon without fiber coated foam blocks. Test results are indicated in Table II below. Table II below clearly indicates that a tampon containing fiber coated foam blocks both absolutely holds more synthetic menses under all pressures and holds a greater multiple of its weight of artificial menses under pressure. Results are listed in Table II.

TABLE II

| Tampon | % Fiber | Foam Weight (g) | Fiber Weight (g) | CLD Weight (g) |
|---|---|---|---|---|
| 1 | 0 | 2.30 | 0 | 0.48 |
| 2 | 20 | 2.10 | 0.53 | 0.48 |

Weight (g) of synthetic menses held under pressure
(Weight to menses held as multiple of tampon weight)

| Tampon | ¼ lb. (13 mm Hg) | ½ lb. (26 mm Hg) | ¾ lb. (39 mm Hg) | 1 lb. (52 mm Hg) |
|---|---|---|---|---|
| 1 | 24.6 (7.1 ×) | 22.6 (6.5 ×) | 19.8 (5.1 ×) | 17.6 (5.1 ×) |
| 2 | 28.3 (7.8 ×) | 25.0 (6.9 ×) | 22.3 (6.2 ×) | 21.0 (5.8 ×) |

Tampons containing the new and absorbent material that is the subject of this invention also show an improved rate of absorbency as can be seen by the sink test, results of which are shown below. The sink time test measures the time it takes for a tampon to become totally saturated with liquid and sink below the surface of a distilled water and food coloring solution. The test requires use of a timer, such as one made by Matheson, Model 219–444; a 600 ml. Matheson beaker, Model 029–561; and 350–400 ml. of distilled water and food coloring. Initially, the 350–400 ml. of test solution are added to the 600 ml. beaker. The tampon is lowered gently into the test solution with its longest axis parallel to the surface of the test solution. On contact with the solution, the timer is started and the time elapsed between contact with the water and the time when the tampon has sunk below the surface of the test solution, or when the tampon contents are completely wetted, is measured. Results are shown in Table III. The sink time test offers some empirical evidence of an improved absorbency rate resulting from use of fiber coating on hydrophilic foam cubes. The unrestrained capacity indicates the total weight of liquid absorbed after the tampon passes the sink time test. This indicates the total unrestrained absorptive capacity of the tampon tested.

The rate of absorbency of tampons are shown in comparisons of wicking rates. Test tampons were inserted in the rubber bladder of a syngyna adjusted to b 13.8 mm Hg. uniform pressure (a pressure simulating inter-vaginal pressure). Artificial menses is induced into the tampon at zero head. The syngyna and tampon are mounted on a Calibrated Instron machine available from Instron Corporation, 2500 Washington Street, Canton, Mass. 02021 and the increase in weight from absorbed synthetic menses is recorded. From this data, a wicking rate can be calculated. The wicking rate of a tampon containing diced ¼ inch cubes of polyester foam is approximately 2.82 gm./minute. The wicking rate of a tampon containing diced ¼ inch cubes of polyester foam coated with 25% by weight Foley Fluff cellulose fibers is 3.88 gm./minute. These figures show that tampons containing the improved absorbent means of the present invention have an improved rate of absorbency which will better prevent flow of menses past the tampon in vivo.

Use of the syngyna also allows for a variety of other tests which will indicate superiority of the use of the absorbent means of the new invention. The dry volume of a tampon can be tested through contrast of water volume, at constant pressure, outside the bladder in the syngyna before and after the dry tampon has been inserted. Similarly, the wet volume of a tampon can also be measured by contrasting, at constant pressure, the volume of water in the syngyna containing a dry tampon and the volume of the water in the syngyna after flooding the tampon with synthetic menses. A squeeze-out test indicates the amount of artificial menses lost with a pressure change on a loaded tampon. A dry tampon is inserted in a rubber bladder of the syngyna and loaded with artificial menses through wicking. Volume changes in the water in the syngyna indicates the volume of the loaded tampon at 0.3 psig (16 mm. Hg.). Syngyna water pressure is then raised to one psi and a certain amount of synthetic menses is squeezed out of the tampon. The amount squeezed out is then measured and shown in Table III below as squeeze out. This indicates that tampons with the improved absorbent means of this invention retain more absorbed menses when subjected to vaginal pressure.

A peristaltic leakage test simulates pressure variations inside the vagina generated by leg movements of the female of involuntary muscle contractions, such as sneezing. In the peristaltic leakage test, a tampon is set in the rubber bladder of the syngyna with the water pressure set at 0.3 psig (16 mm. Hg.) and the tampon is allowed to wick synthetic menses into the tampon until it is fully loaded. At that point, oscillations of pressure are set up in the water surrounding the rubber bladder varying pressure from 0.5 to 1.0 psig (26 to 52 mm. Hg.) for 5 minutes. The amount of artificial menses squeezed out is then measured for weight and is listed in Table III below. The table shows that the tampon containing a fiber covered hydrophilic foam blocks loses significantly less under the pressure changes than tampons having an aggregate absorbent body containing foam blocks without fiber coatings in the peristaltic leakage test, indicating that tampons containing the improved absorbent means of the present invention will leak less menses during leg movements, as in athletic activity.

The tampons containing the new absorbent material that is subject of this invention, fiber coated hydrophilic foam blocks, exhibit significantly more resistance to being crushed under pressure than a tampon containing hydrophilic foam blocks without the fiber coating. Each tampon measured in this test is subject to the following test procedures: insert a tampon into the bladder of the syngyna at a pressure of 0.3 psig (16 mm. Hg.) and measure the total volume of the water contained within the syngyna; add synthetic menses by wicking and increase pressure to one psig (52 mm. Hg.) and measure the total volume of water in the syngyna; subtract total volume at 1.0 psig (52 mm. Hg.) from the total volume at 0.3 psig (16 mm. Hg.) to yield a volume change of the artificial menses loaded (wet) tampon under pressure. The results are listed in Table III below. An examination of the values produced indicates that the tampon containing hydrophilic foam cubes coated with fiber has significantly higher resistance to crush yielding a tampon that is less likely to crush in use and is less likely to lose absorbent capacity. These results are shown in Table III.

TABLE III

| | Foam Weight (g) | Fiber Weight (g) | CLD Weight (g) | Sink Time (Seconds) | Peristaltic Leakage Test (g) | Squeeze Out (ml) | Volume Loss at 1 psi (52 mm Hg) (cc) | Unrestrained Capacity (g) |
|---|---|---|---|---|---|---|---|---|
| Tampon Regular | | | | | | | | |
| 1 | 1.70 | 0 | 0.33 | 35 | 1.6 | 5.1 | 5.9 | 40 |
| 2 | 1.70 | 0.34 | 0.33 | 6 | 0.84 | 2.6 | 3.6 | 46 |
| Tampon Super | | | | | | | | |
| 1 | 2.3 | 0 | 0.48 | 27 | 1.3 | 4.7 | 5.9 | 56 |
| 2 | 2.1 | 0.53 | 0.48 | 7 | 0.53 | 2.2 | 4.9 | 67 |

The examples above are exemplary only and are not intended to limit the invention. As evident to those skilled in the art, the invention includes all variations which fall within the claims which follow.

What is claimed is:

1. An absorbent material consisting of:
   a hydrophilic foam means selected from the group consisting of polyester foam and polyurethane foam; and
   absorbency improvement means at least arrayed on the surface of said foam means, said absorbency improvement means comprising about 5 to about 35% cellulose fibers by weight of said absorbent material wherein said fibers have an average length of at least 1.0 mm and a diameter of 15–45 microns.

2. The material as claimed in claim 1 wherein said fibers have an average length of at least 2.5 mm and a diameter of 35–45 microns.

3. The material as claimed in claim 1 wherein said foam means are shaped as blocks.

4. The material as claimed in claim 3 wherein the edge dimension of said block is 1/16 inches to 1 inch (0.16 to 2.54 cm.).

5. The material as claimed in claim 4 wherein the edge dimension of said blocks is ⅛ inches to ½ inches (0.32 to 1.3 cm.).

6. An absorptive device comprising: an absorbent means comprising an aggregate of individual pieces of absorbent foam means and ancillary absorbent material, wherein the surface of each said foam means is coated with absorbency improvement means, said absorbency improvement means comprising about 5 to about 35% cellulose fibers by weight of said absorbent means wherein said fibers have an average length of at least 1.0 mm and a diameter of 15–45 microns, said aggregate being encased within a flexible fluid permeable overwrap and is wholly contained within the exterior portion of said overwrap, such that substantially none of the absorbent foam means protrude through the exterior portion of the overwrap whereby the exterior surface of the absorbent device is formed by overwrap, said aggregate being flexible and resilient, and said device is soft, highly compressible, comfortable and resilient.

7. An absorptive device, comprising: an absorptive tampon, a tubular inserter, and ejection means operatively associated with said tampon and said inserter for releasing said tampon from said inserter into a body cavity; said tampon having an absorbent means comprising an aggregate of individual pieces of absorbent foam means and ancillary absorbent material, said foam means are coated on at least the surface with absorbency improvement means, said absorbency improvement means comprising about 5 to about 35% cellulose fibers by weight of said absorbent means, wherein said fibers have an average length of at least 1.0 mm and a diameter of 15–45 microns, said aggregate being encased within a flexible fluid-permeable overwrap, said pieces being wholly contained within the exterior portion of said overwrap such that substantially none of the absorbent foam-like material protrudes through the exterior portion of the overwrap whereby the exterior surface of the tampon is formed by the overwrap, said aggregate being flexible and resilient said tampon being resiliently compacted within said inserter, whereby said tampon is easily ejectable, and fluffs out rapidly after in vivo ejection from said inserter to fill the vaginal cross-section.

8. The absorptive device as claimed in claims 6 or 7 wherein said ancillary absorbent material is a polymer.

* * * * *